United States Patent [19]

Medenica

[11] Patent Number: 5,668,119
[45] Date of Patent: Sep. 16, 1997

[54] TOPICAL PHARMACEUTICAL CONTAINING HEPARIN AND METHOD OF TREATMENT

[76] Inventor: Rajko D. Medenica, 2252 Broadway, New York, N.Y. 10024

[21] Appl. No.: 603,861

[22] Filed: Feb. 22, 1996

[51] Int. Cl.⁶ .................................................. A61K 31/725
[52] U.S. Cl. .......................................................... 514/56
[58] Field of Search .................................................. 514/56

[56] References Cited

U.S. PATENT DOCUMENTS

| | | | |
|---|---|---|---|
| 3,232,833 | 2/1966 | Riviere | 514/56 |
| 4,760,131 | 7/1988 | Sundsmo et al. | 530/356 |
| 4,840,626 | 6/1989 | Linsky et al. | 604/364 |
| 4,879,282 | 11/1989 | Saliba, Jr. | 514/56 |
| 4,983,580 | 1/1991 | Gibson | 514/2 |
| 5,272,135 | 12/1993 | Takruri | 514/12 |

FOREIGN PATENT DOCUMENTS

| | | |
|---|---|---|
| 746855 | 8/1970 | Belgium . |
| 154447 | 9/1985 | European Pat. Off. . |
| 28 06 515 | 8/1979 | Germany . |
| 30 20 220 | 12/1981 | Germany . |
| 30 49 445 | 7/1982 | Germany . |
| 512246 | 10/1971 | Switzerland . |
| 1080824A | 3/1984 | U.S.S.R. . |
| 891554 | 3/1962 | United Kingdom . |

*Primary Examiner*—Kathleen K. Fonda
*Attorney, Agent, or Firm*—DeWitt Ross & Stevens SC

[57] ABSTRACT

A topical pharmaceutical for the treatment of thrombosis or hematoma, and a method for the topical treatment of thrombosis or hematoma, are described. The topical pharmaceutical contains effective thrombosis-inhibiting amounts of heparin, allantoin, thymol, and mefenamic acid dispersed in a pharmaceutically-acceptable carrier for topical administration. The method of treating thrombosis and hematoma includes externally contacting the area with an effective amount of a composition containing heparin, allantoin, thymol, and mefenamic acid.

21 Claims, No Drawings

TOPICAL PHARMACEUTICAL CONTAINING HEPARIN AND METHOD OF TREATMENT

FIELD OF THE INVENTION

The present invention relates to topical pharmaceuticals containing heparin for the treatment of thrombosis, hematoma, post-cytopenia hematoma, traumatic hematoma and lesions, chronic venestasia, diffuse hematoma patches and the like.

DESCRIPTION OF THE PRIOR ART

Heparin is a well known and frequently used intravenous anti-coagulant. Chemically, heparin is classified as a glycosaminoglycan. Glycosaminoglycans are the polysaccharide portions of proteoglycans. The heparin polysaccharide backbone is composed of repeating units of D-glucosamine and either L-iduronic or D-glucuronic acids. The polysaccharide backbone further includes a heterogeneous mixture of negatively charged carboxylate and sulfate functional groups which gives the molecule an overall anionic character at physiological pH. Heparin is biosynthesized and stored in mast cells of various tissues, most notably liver, lung, and gut. Heparin exerts its anti-coagulant effect by increasing the rate of formation of an irreversible complex between thrombin and antithrombin III.

The U.S. patent literature contains various references to pharmaceutical compositions containing heparin in combination with other active ingredients to treat many different medical conditions. For instance, U.S. Pat. No. 3,232,833 to Riviere and U.S. Pat. No. 4,983,580 to Gibson, describe ophthalmologic pharmaceuticals containing heparin. The Riviere patent describes an ophthalmologic collyrium containing a compound capable of liberating the heparin ion, a vaso-constricter, and a third ingredient. This medicament is to be used for the treatment of eye complaints such as conjunctivitis, keratitis, and corneal vascularizations. The Gibson reference describes a corneal mortar for treating wounds to the corneal stroma. Here, the pharmaceutical is formulated with a sufficiently high viscosity such that it is retained within a corneal wound under physiological conditions. This pharmaceutical is primarily used in promoting the healing of corneal incisions made during keratorefractive surgery.

U.S. Pat. No. 4,760,131 to Sundsmo et al. describes a soft tissue wound-healing pharmaceutical which contains fibrillar collagen, heparin, and un-degranulated platelets dispersed within an aqueous carrier. The composition is applied topically to soft tissue wounds. The composition can also be incorporated into a solid carrier, such as a wound dressing. If applied to a depressed wound, this reference describes formulating the above ingredients into an ointment or gel which can be packed directly into the wound.

A wound dressing in which the fabric of the dressing has heparin incorporated therein is described in U.S. Pat. No. 4,840,626 to Linsky et al. This wound dressing is designed for internal, surgical use for the prevention of post-surgical adhesions. In surgical applications, the heparin-impregnated fabric forms an adhesion-preventative barrier which is then substantially absorbed by the patient's body within approximately thirty days. The presence of the heparin-impregnated dressing is reported to significantly lessen the formation of surgical adhesions.

Several uses for heparin and heparin-like compounds are described in U.S. Pat. No. 4,879,282 to Saliba, Jr. Among the several uses described in this patent are the use of heparin for preserving and healing cells and cell functions arising from transplantation, circumcision, dermatitis, fissures, and fistulas. This reference describes the topical application of heparin either in solution or in the form of a cream or aerosol. Heparin is present in this formulation in an amount ranging from 1,500 to 5,000 IU per milliliter at a pH of about 5.5. No other active ingredients are included in the formulation.

U.S. Pat. No. 5,272,135 to Takruri describes a method for inhibiting the oxidation of a polypeptide in a liquid or semi-solid pharmaceutical preparation. Inhibition of oxidation of such formulations is accomplished by the addition of the amino acid methionine into the formulation. The free methionine functions to inhibit the oxidation of methionine residues contained within the active polypeptide. More specifically, Takruri describes the use of the method for preserving cornea storage media which includes heparin sulfate.

Several foreign patent references also describe the use of heparin in topical pharmaceutical formulations. For instance, British Patent No. 997,727 describes aqueous solutions of heparin dispersed in a conventional ointment base. This reference specifically describes an ointment for the treatment of thrombosis which contains approximately 1% by weight of active substances. These active substances include heparin, and a calcium complex sodium salt of a polysulphuric acid ester. The formulation also includes p-chloro-m-cresol, methyl-p-hydroxybenzoate, isopropyl-p-hydroxybenzoate, glycerine, Tween 60, sodium alginate, and white paraffin, stearyl alcohol, and isopropyl myristate.

Patent No. 891,554 (Great Britain) describes a galenic suppository which contains heparin salts. Here, heparin salts are incorporated into conventional semi-solid bases such as cocoa butter, wax, or glyceric esters of saturated fatty acids. The authors of this reference have found that the general anti-coagulant action of heparin does not manifest itself when the salts are administered in the form of suppositories. However, the anti-inflammatory action of the heparin salts is maintained. This renders the heparin-containing suppositories suitable for the treatment of hemorrhoids.

Swiss Patent No. 512,246 describes the preparation of antibiotic heparinates which have prolonged anti-coagulant and anti-bacterial activity when applied topically. These antibiotic heparinates are particularly active against gram-negative germs.

Two German patent references to Eckertt, DE 30 20 220 and DE 30 49 445, describe the preparation of heparin salts with organic bases. The abstracts to these German-language references note that the salts show good absorption properties when applied topically in the form of ointments, emulsions, solutions, or gels.

Another German reference, Offenlegungsschrift 28 06 515, describes the formation of amorphous sodium salts of heparin. The amorphous salts are produced by precipitation of sodium heparin from an aqueous solution by the addition of an excess quantity of isopropanol. The resultant product is easily distributed in nonaqueous media such as ointments or suppositories for the treatment of hemorrhoids.

Belgium Patent No. 746,855 describes the use of pyridoxine heparinates in injectable solutions, tablets, suppositories, and ointments for topical application. These compositions are described as containing approximately 5% pyridoxine heparinate.

Soviet Union Patent 1,080,824A describes the treatment of serum-positive primary syphilis using penicillin in combination with topical application of an ointment containing heparin. This course of therapy is alleged to accelerate the regression of the primary syphilis, with a resultant shortened duration of therapy.

European Patent Application No. 154,447 describes compositions for promoting wound healing which include a suspension of collagen and a glucosaminoglycan such as heparin, heparin sulfate, or an alginate. The preferred composition is a colloidal suspension containing 280 meq/ml of heparin.

None of the above references, taken alone or in any combination, are seen as describing the presently described topical pharmaceutical.

SUMMARY OF THE INVENTION

A principal aim of the present invention is to provide a topical pharmaceutical effective for the treatment of thrombosis, hematoma, post-cytopenia hematoma, traumatic hematoma, chronic venestasia, diffuse hematoma patches and the like, which contains effective amounts of heparin, allantoin, thymol, and mefenamic acid.

It is a further aim of the present invention to provide a topical pharmaceutical for the treatment of the above conditions which can be formulated in the form of a cream, an ointment, a gel, and the like.

It is a still further aim of the present invention to provide a topical pharmaceutical which contains, as a primary active ingredient, heparin, heparinates, or heparinoids dispersed in a pharmaceutically suitable carrier for topical application.

Yet another aim of the present invention is to provide a topical pharmaceutical containing heparin which is effective to inhibit thrombosis and hematoma in human patients undergoing long-term intravenous treatments, parenteral feeding, and the like.

These and other aims and objects of the present invention will become apparent upon a reading of the detailed description, below.

The present invention includes a topical pharmaceutical which is effective for the treatment of thrombosis, hematoma due to multiple phlebotomy, venipuncture, or cytopenia, traumatic hematoma (i.e., bruises, lesions, and the like), chronic venestasia, and hematoma patches due to advancing age comprising a therapeutically effective amount of heparin, allantoin, thymol, and mefenamic acid, dispersed in a pharmaceutically-acceptable carrier.

The present invention also encompasses a topical pharmaceutical effective for the treatment of the above-noted maladies which comprises from about 100 to about 300 I.U. heparin per gram total weight, from about 0.1 to about 3.0 weight percent allantoin, from about 0.1 to about 1.0 weight percent thymol, and from about 1.0 to about 5.0 weight percent mefenamic acid dispersed in a pharmaceutically-acceptable carrier for topical administration.

The present invention further includes a method of topically treating thrombosis, hematoma due to multiple phlebotomy, venipuncture, or cytopenia, traumatic hematoma (i.e., bruises, lesions, and the like), chronic venestasia, and hematoma patches due to advancing age which comprises externally contacting the affected area with an effective amount of a composition comprising a therapeutically effective amount of heparin, allantoin, thymol, and mefenamic acid, dispersed in a pharmaceutically-acceptable carrier for topical application.

As noted immediately above, the composition of the present invention is effective to treat a wide range of thrombocytic conditions. For instance, the composition can be used to treat hematoma after multiple phlebotomy, peripheral venous thrombosis, traumatic hematoma, post-thrombocytopenia hematoma, chronic venestasia, diffused hematoma patches, and other thromboses.

It is preferred that the topical composition of the present invention be liberally applied to the affected area at least twice a day over a period of several days. Topical application of the formulation up to four times a day does not change prothrombin time (PT) or partial thromboplastin time (PTT), yet significantly inhibits thrombosis.

As a consequence, the present topical pharmaceutical is greatly beneficial to patients who are subjected to multiple venipuncture, phlebotomy, multiple IV infusion of chemotherapy, or parenteral nutrition. The presently described pharmaceutical also aids in the healing of various hematomas and also inhibits venous inflammation, thereby assuring the permeability of the vein for intravenous injection.

DETAILED DESCRIPTION OF THE INVENTION

The presently described topical pharmaceutical is generally formulated as follows:

To formulate an ointment for topical administration, conventional anhydrous ointment base is heated to 60° C. along with the addition of an emulsifier and a preservative, if desired. A typical emulsifier would be polysorbate 80, although many equivalent emulsifiers are known and can be used with equal success. Typical preservatives would include butylated hydroxy toluene (BHT) and/or butylated hydroxy anisole (BHA). Water heated to 60° C. is then added to the ointment base with constant stirring until a smooth and suitably viscous consistency is obtained. The ointment base is then removed from the heat source and constantly stirred until homogenous.

At this point, heparin, allantoin, thymol, and mefenamic acid are added to the ointment base with constant stirring. The combination of these four active ingredients results in a synergistic action which yields remarkable clinical results. As discussed more completely below, allantoin is the diureide of glyoxalic acid. Allantoin is a product of purine metabolism which is excreted in the urine of many mammals, but not in *Homo sapiens* or the higher apes.

Thymol is a phenol extracted from thyme oil. It has known uses as an anti-bacterial or antifungal agent, and also has anthelmintic and carminative action. Mefenamic acid is an analgesic, which also has anti-inflammatory and antipyretic effects. As noted above, heparin is a well known anti-coagulant.

As used herein, the term "heparin" refers to any type of pharmaceutically-acceptable heparin, heparinate, or heparinoid. Consequently, as used herein, the term "heparin" includes complexed and uncomplexed heparin, heparin salts such as sodium heparin, potassium heparin, calcium heparin and magnesium heparin, heparin esters, and heparinic acids. Such heparin compounds are widely available from a large number of commercial sources. For instance, calcium heparin is sold under the tradenames CALCIPARINE and ECASOLV, magnesium heparin is available under the tradename CUTHEPARINE, and sodium heparin is available many tradenames including HEPRINAR and HEPSAL. Commercially available heparin is isolated from beef lung or pork intestinal mucosa and generally has a molecular weight between 6 and 30 kD.

Likewise, allantoin, thymol, and mefenamic acid are widely available in commercial markets.

Allantoin ((2,5-dioxo-4-imidazolidinyl)urea or 5-ureidohydantoin, also known as glyoxyldiureide and codianine) is sold under various tradenames including PSORALON and SEPTALAN. It is a natural product of purine metabolism. It can be prepared synthetically by the oxidation of uric acid with alkaline potassium permanganate, or by heating urea with dichloroacetic acid.

Thymol (5-methyl-2-(1-methylethyl)phenol or 1-methyl-3-hydroxy-4-isopropylbenzene, also known as thyme camphor) is a natural product obtained from the essential oil of *Thymus vulgaris* and other plant species. It can be produced synthetically from p-cymene, piperitone, or m-cresol. It has a very characteristic pungent odor and a caustic taste. Thymol has known antiseptic and antifungal qualities, and has been used in animals as an anthelmintic against nematodes. It is widely available commercially from a number of suppliers.

Mefenamic acid (2-[(2,3-dimethylphenyl)amino]-benzoic acid) is available commercially under the tradenames BAFHAMERITIN-M, BONABOL, COSLAN, LYSALGO, NAMPHEN, PARKEMED, PONALAR, PONSTAN, PONSTEL, PONSTIL, PONSTYL, PONTAL, TANSTON, and VIALIDON. It is widely available in the form of its sodium salt.

The above ingredients are added to the ointment base slowly and with constant stirring. The ointment is then allowed to come to room temperature and packaged accordingly. Aseptic conditions should be maintained throughout the manufacturing process.

The combination of these active ingredients has a synergistic effect which allows the active ingredients to efficiently penetrate tissues when applied topically.

In addition to an ointment formulation, the above-described active ingredients can also be formulated in any known pharmaceutically-acceptable carrier for topical application, including cream bases, lotions, gels, aerosols, and the like. The preferred formulations are those wherein the heparin, allantoin, thymol, and mefenamic acid are dispersed within cream bases and ointment bases.

A typical cream or ointment-type carrier for topical application which can be used in the present invention includes a mixture of water, glycerin, propylene glycol, and methylparaben. Topical carriers may also include other conventional emulsifiers and emollients including alginates, glyceryl stearate, PEG-100 stearate, cetyl alcohol, propylparaben, butylparaben, sorbitols, polyethoxylated anhydrosorbitol monostearate (TWEEN), white soft paraffin (VASELINE), triethanolamine, aloe vera extract, lanolin, cocoa butter, and the like. Suitable topical carriers are well known to the skilled artisan. A typical ointment-type base, provided herein for exemplary purposes only, to aid in a complete understanding of the present invention, contains 20 parts glycerin, 12 parts TWEEN 60, 1 part sodium alginate, 34 parts VASELINE, 20 parts stearyl alcohol, and 10 parts isopropyl myristate, dispersed in about 100 parts water. Topical carriers with different viscosities and hand-feel are known to the art.

The above active ingredients are dispersed within the pharmaceutically-acceptable carrier in therapeutically effective amounts to treat thrombosis, hematoma, chronic venestasia, and the other maladies described above. Preferably, the topical pharmaceutical of the present invention contains (per gram total weight) from about 100 to about 300 I.U. heparin, from about 0.1 to about 3.0 weight percent allantoin, from about 0.1 to about 1.0 weight percent thymol, and from about 1.0 to about 5.0 weight percent mefenamic acid.

A method to treat thrombosis, hematoma, post-cytopenia hematoma, traumatic hematoma and lesions, chronic venestasia, diffuse hematoma patches, and the like entails liberally applying the above-described topical pharmaceutical to an effected area at least twice a day for several consecutive days.

EXAMPLES

A heparin cream or ointment prepared as described above was used clinically in a sample of patients presenting various thromboses and hematomas.

An initial testing of the presently described pharmaceutical was performed on 86 volunteers (ages 3–80). The above-described ointment formulation was topically applied 4 times a day for 5 consecutive days. No side effects were seen and the heparin formulation did not change the prothrombin time (PT) or partial thromboplastin time (PTT) of the test subjects. The formulation is well absorbed in 10–15 minutes, after which the skin remains dry. Because the formulation does not leave any greasy residue, it is not distracting to the user.

A particular motivation to develop this formulation was for use with patients who are undergoing multiple venipuncture, phlebotomy, multiple IV infusion of chemotherapy, or parenteral nutrition. Inhibition of thrombosis and hematomas, along with the prevention of venous inflammation assures the permeability of veins for further medical treatments. In particular, use of the present topical pharmaceutical allows veins to be maintained in excellent condition in patients who are undergoing multiple chemotherapy. Considerable reduction of the hematomas on the site of the venipunctures was seen in the following patient study. The formulation can also be used for the prevention and maintenance of venous deterioration and catheterization after long term therapy. In this manner, a vein can be maintained in acceptable condition for further IV therapy or phlebotomy.

The following study included 271 patients (age 3–98). The age breakdown of the patients treated is as follows:

TABLE A

| RANGE OF AGE | NUMBER OF PATIENTS |
|---|---|
| 3–10 | 11 |
| 10–20 | 28 |
| 20–30 | 17 |
| 30–40 | 78 |
| 40–50 | 53 |
| 50–60 | 28 |
| 60–70 | 37 |
| 70–80 | 18 |
| 80–98 | 11 |

These patients suffered from different forms of venous lesions and hematoma, including subcutaneous or intramuscular infiltration and different hematoma patches. The distribution of these lesions was as follows:

TABLE B

| DISEASE | NUMBER OF PATIENTS |
|---|---|
| Hematoma After Multiple Phlebotomy | 89 |
| Peripheral Venous Thrombosis | 23 |
| Hematoma of Traumatic Origin | 57 |
| Hematoma Post-Thrombocytopenia | 39 |
| Chronic Venestasia | 46 |
| Diffuse Hematoma Patches | 17 |

Different sizes of hematoma lesions were treated. The lesions were measured before beginning therapy. The size of the lesion after venipuncture was estimated and peripheral thrombophlebitis was also estimated. These initial measurements are tabulated in Table C.

TABLE C

| HEMATOMA IN CENTIMETERS | NUMBER OF PATIENTS |
|---|---|
| Less than 1 cm | 49 |
| 1 cm–3 cm | 27 |
| 3 cm–5 cm | 56 |
| 5 cm–8 cm | 41 |
| 8 cm–15 cm | 27 |
| 16 cm–20 cm | 33 |
| 20 cm–30 cm | 38 |

The lesions were then treated with the above-described ointment formulation. The formulation was applied by covering the entire lesion with a very thin coat accompanied with a light massage for about 30 seconds. The ointment absorbed rapidly and dried in approximately 30 minutes. This was repeated every 4 hours during the period when the patient was not sleeping. For the peripheral venous thrombosis, the formulation was applied over the vein and very gently massaged into the skin. The response of the various hematomas is categorized in Table D:

TABLE D

| NAME OF DISEASE | # OF PTS | DISAPPEARANCE OF LESION | | | | | |
|---|---|---|---|---|---|---|---|
| | | DAY 1 | DAY 2 | DAY 3 | DAY 4 | DAY 5 | DAY 15 |
| Hematoma of Multiple Phlebotomy | 89 | 72 | 16 | 1 | 0 | 0 | 0 |
| Peripheral Venous Thrombosis | 23 | 0 | 4 | 8 | 7 | 2 | 2 |
| Hematoma of Traumatic Origin | 57 | 16 | 23 | 10 | 5 | 3 | 0 |
| Hematoma Post-Thrombocytopenia | 39 | 22 | 7 | 10 | 0 | 0 | 0 |
| Chronic Venestasia | 46 | 2 | 8 | 12 | 13 | 6 | 5 |
| Diffuse Hematoma Patches | 17 | 6 | 8 | 3 | 0 | 0 | 0 |

Laboratory tests included complete blood count, prothrombin time (PT), and partial thromboplastin time (PTT) at the beginning and end of treatment. There were no significant changes in the value of these laboratory tests for any of the patients tested. No side effects were observed.

The above patient samplings were compared with control groups comprising 6 patients in each of the disease categories listed in Table D (36 control patients in total). In the control groups, no therapy was given and the patient was observed for 15 days. The results for the control groups are depicted in Table E

TABLE E

| NAME OF DISEASE | STATUS |
|---|---|
| Hematoma of Multiple Phlebotomy | 5–15 + Days: 3 patients displayed marked hematoma. |
| Peripheral Venous Thrombosis | One (1) patient enjoyed spontaneous remission. The remaining 5 patients suffered marked deterioration. |
| Hematoma of Traumatic Origin | 6–15 + Days: 2 patients recovered, 4 patients displayed marked hematoma. |
| Hematoma Post-Thrombocytopenia | 10–15 + Days: 2 patients died. The remaining 4 patients all remained diseased. |
| Chronic Venestasia | Lesions persisted after 15 Days. |

TABLE E-continued

| NAME OF DISEASE | STATUS |
|---|---|
| Diffuse Hematoma Patches | 10 Days: 38% of patches disappeared spontaneously in 2 patients; 4 patients progressively deteriorated. |

A comparison of the experimental patient group with the control groups demonstrates the considerable healing activity of the presently described medication. The topical pharmaceutical described and claimed herein is a successful medication for thrombosis, hematomas and venous damage caused by phlebotomy or any traumatic origin.

The present invention is not limited to the embodiments described above, but encompasses all variations and equivalents thereof as fall within the scope of the attached claims.

What is claimed is:

1. A topical pharmaceutical composition effective for the treatment of thrombosis or hematomas comprising a therapeutically effective amount of each of heparin, allantoin, thymol, and mefenamic acid, dispersed in a pharmaceutically-acceptable carrier.

2. The composition of claim 1 wherein the hematoma is selected from the group consisting of post-traumatic hematoma, post-cytopenia hematoma, chronic venestasia, and diffuse hematoma patches.

3. The topical pharmaceutical composition according to claim 1, wherein heparin is present in an amount of from about 100 to about 300 I.U. per gram total weight.

4. The topical pharmaceutical composition according to claim 3 containing from about 0.1 to about 3.0 weight percent allantoin; from about 0.1 to about 1.0 weight percent thymol; and from about 1.0 to about 5.0 weight percent mefenamic acid.

5. The topical pharmaceutical composition according to claim 3, wherein heparin is present in an amount of about 200 I.U. per gram total weight.

6. The topical pharmaceutical composition according to claim 1, wherein the pharmaceutically-acceptable carrier is selected from the group consisting of cream bases and ointment bases.

7. The topical pharmaceutical composition according to claim 1, further comprising an anti-oxidant preservative.

8. The topical pharmaceutical composition according to claim 7, wherein the anti-oxidant preservative is selected from the group consisting of butylated hydroxytoluene and butylated hyrdroxyanisole.

9. The topical pharmaceutical composition according to claim 7, further comprising an emulsifier.

10. The topical pharmaceutical composition according to claim 9, wherein the emulsifier is polysorbate 80.

11. A topical pharmaceutical composition effective for the treatment of thrombosis, hematomas of any etiology, including post-traumatic hematoma and post-cytopenia hematoma, chronic venestasia, and diffuse hematoma patches comprising:

from about 100 to about 300 I.U. heparin per gram total weight;

from about 0.1 to about 3.0 weight percent allantoin;

from about 0.1 to about 1.0 weight percent thymol; and from about 1.0 to about 5.0 weight percent mefenamic acid, dispersed in a pharmaceutically-acceptable carrier.

12. The composition of claim 11 wherein the hematoma is selected from the group consisting of post-traumatic hematoma, post-cytopenia hematoma, chronic venestasia, and diffuse hematoma patches.

13. The topical pharmaceutical composition according to claim 11, wherein the pharmaceutically-acceptable carrier is selected from the group consisting of cream bases and ointment bases.

14. The topical pharmaceutical composition according to claim 11, further comprising an anti-oxidant preservative.

15. The topical pharmaceutical composition according to claim 14, wherein the anti-oxidant preservative is selected from the group consisting of butylated hydroxytoluene and butylated hyrdroxyanisole.

16. The topical pharmaceutical composition according to claim 14, further comprising an emulsifier.

17. The topical pharmaceutical composition according to claim 16, wherein the emulsifier is polysorbate 80.

18. A method of topically treating an area affected by thrombosis or hematomas in a patient in need thereof comprising:

externally contacting the area with an effective amount of a composition comprising a therapeutically effective amount of each of heparin, allantoin, thymol, and mefenamic acid, dispersed in a pharmaceutically-acceptable carrier.

19. The method of claim 18 wherein the hematoma is selected from the group consisting of post-traumatic hematoma, post-cytopenia hematoma, chronic venestasia, and diffuse hematoma patches.

20. The method according to claim 18, wherein the patient is a human.

21. The method according to claim 20, wherein the human patient is externally contacted with a composition comprising:

from 100 to 300 I.U. heparin per gram total weight;

from 0.1 to 3.0 weight percent allantoin;

from 0.1 to 1.0 weight percent thymol; and from 1.0 to 5.0 weight percent mefenamic acid.

* * * * *